United States Patent
Smith et al.

(10) Patent No.: US 8,709,187 B2
(45) Date of Patent: Apr. 29, 2014

(54) METHOD OF FORMING A CONDUIT

(75) Inventors: Daniel John Smith, Auckland (NZ);
Nathan Lee Gray, Auckland (NZ);
Luke Jeremy Gallagher, Auckland
(NZ); Kieran James Hatcher, Auckland
(NZ); Kristopher Poh Ming Laurent,
Auckland (NZ)

(73) Assignee: Fisher & Paykel Healthcare Limited,
Auckland (NZ)

( * ) Notice: Subject to any disclaimer, the term of this
patent is extended or adjusted under 35
U.S.C. 154(b) by 397 days.

(21) Appl. No.: 12/269,946

(22) Filed: Nov. 13, 2008

(65) Prior Publication Data

US 2009/0065119 A1 Mar. 12, 2009

Related U.S. Application Data

(62) Division of application No. 10/527,032, filed as application No. PCT/NZ03/00204 on Sep. 11, 2003.

(30) Foreign Application Priority Data

Sep. 11, 2002 (NZ) .......................... 521364
Oct. 31, 2002 (NZ) .......................... 522310

(51) Int. Cl.
*B31C 1/00* (2006.01)

(52) U.S. Cl.
USPC ........ 156/184; 156/191; 156/192; 264/271.1; 264/272.11

(58) Field of Classification Search
USPC ......... 156/143, 184, 185, 187, 191, 192, 195; 264/271.1, 272.11
See application file for complete search history.

(56) References Cited

U.S. PATENT DOCUMENTS

| 2,250,430 | A | | 7/1941 | Wade | |
| 2,489,503 | A | * | 11/1949 | Sampson et al. | 156/429 |
| 2,748,830 | A | | 6/1956 | Nash et al. | |
| 2,810,400 | A | * | 10/1957 | Hewitt | 138/122 |
| 3,317,657 | A | | 5/1967 | Eisler | |
| 3,477,891 | A | | 11/1969 | Hawerkamp | |
| 3,737,997 | A | | 6/1973 | Davis | |
| 3,902,938 | A | | 9/1975 | Eller et al. | |
| 4,012,272 | A | * | 3/1977 | Tiner | 156/429 |

(Continued)

FOREIGN PATENT DOCUMENTS

| AU | 194 74 68122 | 4/1974 |
| DE | 198 48 172 | 4/2000 |

(Continued)

OTHER PUBLICATIONS

Hytrel thermoplastic polyester elastomer from E.I. du Pont de Nemours and Company; Sixty-three (63) pages; Copyright 2000.

*Primary Examiner* — Christopher Schatz
(74) *Attorney, Agent, or Firm* — Knobbe, Martens, Olson & Bear, LLP

(57) ABSTRACT

A method of continuously forming heated conduit includes performing a tape for winding onto a spiral pipeline former. At least one conductor is positioned adjacent to the centerline of and parallel with a thin polymer ribbon. The ribbon is folded in half to encapsulate the conductors. The folded ribbon is thermally welded to itself. The folded, welded, ribbon is passed through a creaser, which forms a crease midway across the folded ribbon. The creased pre-formed ribbon is formed into a conduit in a continuous process on a spiral pipeline former.

17 Claims, 10 Drawing Sheets

(56) References Cited

U.S. PATENT DOCUMENTS

| | | |
|---|---|---|
| 4,294,636 A | 10/1981 | Vitellaro |
| 4,343,672 A | 8/1982 | Kanao |
| 4,468,089 A | 8/1984 | Brorein |
| 4,650,406 A | 3/1987 | Peters |
| 4,674,999 A | 6/1987 | Francis |
| 4,708,756 A | 11/1987 | Busen et al. |
| 4,897,030 A | 1/1990 | Vajtay |
| 4,948,638 A | 8/1990 | Francis |
| 4,950,511 A | 8/1990 | Francis |
| 5,342,991 A | 8/1994 | Xu et al. |
| 2,361,374 A | 10/1994 | Abbott |
| 5,454,061 A | 9/1995 | Carlson |
| 5,502,287 A | 3/1996 | Nguyen |
| 5,607,529 A | 3/1997 | Adamczyk et al. |
| 5,637,168 A | 6/1997 | Carlson |
| 5,848,223 A | 12/1998 | Carlson |
| 6,190,480 B1 | 2/2001 | Carlson |
| 6,219,490 B1 | 4/2001 | Gibertoni et al. |
| 6,769,431 B2 | 8/2004 | Smith et al. |

FOREIGN PATENT DOCUMENTS

| | | |
|---|---|---|
| EP | 1 153 627 | 5/2001 |
| GB | 2 065 430 | 1/1981 |
| GB | 2 247 857 | 3/1992 |
| JP | 8-52797 | 2/1996 |
| JP | 11-141138 | 5/1999 |

* cited by examiner

METHOD OF FORMING A CONDUIT

CROSS-REFERENCE

This patent application is a divisional of U.S. patent application Ser. No. 10/527,032, filed Oct. 6, 2005, and entitled "CONDUITS AND METHODS OF FORMING" which in turn, is a national phase filing of PCT/NZ03/000204, filed Sep. 11, 2003 published as WO 2004/024429, and entitled "CONDUITS AND METHOD OF FORMING". These applications are hereby incorporated by reference.

BACKGROUND TO THE INVENTION

1. Field of the Invention

The present invention relates to components for breathing circuits and in particular to conduits for use in the limbs of breathing circuits. The invention also relates to methods of manufacturing such conduits.

2. Summary of the Prior Art

In assisted breathing, particularly in medical applications, gases are supplied and returned through conduits. Such conduits are ideally light and flexible to ensure the greatest level of comfort for the patient. In the prior art, thin walled conduits are known which include helical or annular reinforcing ribs which act to give the conduit better resistance to crushing and pinching, while still allowing the conduit to be light and flexible. An example of one such conduit is shown in FIG. 1.

It is advantageous to manufacture this type of conduit as a continuous process. In the prior art this is achieved by spiral winding of a thin polymer tape onto a former such that the edges of adjacent layers overlap a small amount. A bead of molten polymer is then applied over the top of the overlapping edges welding them together and simultaneously forming the helical reinforcing ribs. To form a heated conduit, one or more heater wires are positioned on the polymer tape or film as the tape is drawn onto the former. The wires must be accurately positioned adjacent the free edge of the tape, to be covered by a subsequent turn and then by the molten bead. Continuous accurate positioning can be difficult to achieve, and if it is lost the wire can be exposed to either the inside or outside of the tube instead of being encapsulated in the conduit wall.

SUMMARY OF THE INVENTION

It is an object of the present invention to provide a conduit, with particular application to the limbs of a breathing circuit, which will at least go some way towards improving on the above or which will at least provide the public and the medical profession with a useful choice, and/or to provide a method of manufacturing a conduit which will at least go some way towards providing the public and manufacturers with a useful choice.

In a first aspect the invention may broadly be said to consist in a method of forming a film comprising:
providing a thin polymer ribbon,
positioning at least one conductor adjacent to and substantially parallel with said ribbon,
folding said ribbon substantially in half parallel with said ribbon such that said at least one conductor is adjacent to, and encapsulated in said fold, and thermally welding said folded ribbon to permanently encapsulate said at least one conductor.

Preferably said at least one conductor is a pair of conductors, and said conductors are positioned parallel and closely spaced and said ribbon is folded adjacent one said conductor; such that a first of said pair of conductors is adjacent to and encapsulated in said fold, and
a second of said pair of conductors is spaced from said first conductor and encapsulated in said fold.

Preferably said thermal welding comprises passing said folded ribbon between a pair of heated rollers,
said rollers applying pressure to squeeze said folded ribbon together.

Preferably at least one of said rollers includes a groove for at least partially receiving each of said at least one conductor and the layer of ribbon over it.

Preferably said method further comprises forming a crease substantially midway along said folded ribbon, said crease being substantially parallel with said ribbon;
forming said crease while said ribbon is softened following said thermal welding occurring.

Preferably said crease is formed by passing said folded film through at least one set of crease rollers,
said rollers in a creasing region shaped according to the profile of said crease.

In a further aspect the invention may broadly be said to consist in a method of forming a film comprising:
providing a thin polymer ribbon,
heating said ribbon to soften said ribbon, forming a crease approximately midway across said ribbon, said crease being substantially parallel with said ribbon, and
winding said creased ribbon onto a spool Preferably said crease is formed by passing said film through at least one set of crease rollers,
said crease rollers in a creasing region shaped according to the profile of said crease.

In a further aspect the invention may broadly be said to consist in a method of continuously forming a conduit comprising:
providing a thin polymer ribbon,
positioning at least one conductor adjacent to and substantially parallel with said ribbon,
folding said ribbon substantially in half parallel with said ribbon such that said at least one conductor is adjacent to, and encapsulated in said fold, and thermally welding said folded ribbon to permanently encapsulate said at least one conductor,
supplying said folded ribbon having "leading" and "trailing" lateral edges, spirally around a former rotating and advancing said conduit, with the leading edge of each turn of ribbon overlapping the trailing edge of a previous turn of ribbon on the former and the trailing edge of each turn underlapping the leading edge of a succeeding turn, and
applying a bead of molten plastic material to said lapping edges of adjacent turns of ribbon, such that said bead welds said adjacent edges.

Preferably said at least one conductor is a pair of conductors, and said conductors are positioned parallel and closely spaced and said ribbon is folded adjacent one said conductor; such that a first of said pair of conductors is adjacent to and encapsulated in said fold, and
a second of said pair of conductors is spaced from said first conductor and encapsulated in said fold.

Preferably said thermal welding includes passing said folded ribbon between a pair of heated rollers,
said rollers applying pressure to squeeze said folded ribbon together.

Preferably at least one of said rollers includes a groove for at least partially receiving each of said at least one conductor and the layer of ribbon over it.

Preferably said method further comprises forming a crease substantially midway along said folded ribbon, said crease being substantially parallel with said ribbon;

forming said crease while said ribbon is softened following said thermal welding occurring.

Preferably said crease is formed by passing said folded film through at least one set of crease rollers, said crease rollers in a creasing region shaped according to the profile of said crease.

In a further aspect the invention may broadly be said to consist in a method of continuously forming conduit comprising:

providing a thin polymer ribbon, heating said ribbon to soften said ribbon, forming a crease approximately midway across said ribbon, said crease being substantially parallel with said ribbon, supplying said folded ribbon having "leading" and trailing" lateral edges, spirally around a former rotating and advancing said conduit, with the leading edge of each turn of ribbon overlapping the trailing edge of a previous turn of ribbon on the former and the trailing edge of each turn underlapping the leading edge of a succeeding turn, and applying a bead of molten plastic material to said lapping edges of adjacent turns of ribbon, such that said bead welds said adjacent edges.

Preferably said crease is formed by passing said folded film through at least one set of crease rollers, said crease rollers in a creasing region shaped according to the profile of said crease.

In a further aspect the invention may broadly be said to consist in an apparatus for forming a film comprising:

a means for supplying a thin polymer ribbon, at least one spool for supplying at least one thin conductor, at a first position adjacent to and substantially parallel with said ribbon, a folding means to fold said ribbon substantially in half such that said at least one conductor is adjacent to and encapsulated by said folded ribbon, a thermal welding means adapted to weld said folded film and permanently encapsulate said at least one conductor.

Preferably said thermal welding means includes a pair of heated rollers, said rollers applying pressure to squeeze said folded ribbon together.

Preferably at least one of said rollers includes a groove for at least partially receiving each of said at least one conductor and the layer of ribbon over it.

In a further aspect the invention may broadly be said to consist in an apparatus for forming a film comprising:

a means for supplying a thin polymer ribbon, a heating means for heating said thin polymer ribbon, a creasing means for forming a crease in said ribbon after being heated by said heating means, approximately midway across said ribbon, said crease being substantially parallel with said ribbon, and a spool for receiving said creased ribbon.

Preferably said apparatus further comprises:

a creasing means for forming a crease in said ribbon approximately midway across said ribbon, said crease being substantially parallel with said ribbon.

In a further aspect the invention may broadly be said to consist in an apparatus for continuously forming conduit comprising:

a means for supplying a thin polymer ribbon, at least one spool for supplying at least one thin conductor, at a first position adjacent to and substantially parallel with said ribbon, a folding means to fold said ribbon substantially in half such that said at least one conductor is adjacent to and encapsulated by said folded ribbon, a thermal welding means adapted to weld said folded film and permanently encapsulate said at least one conductor, a means for delivering said folded ribbon having "leading" and trailing" lateral edges, spirally around a former rotating and advancing said conduit, with the leading edge of each turn of ribbon overlapping the trailing edge of a previous turn of ribbon on the former and the trailing edge of each turn underlapping the leading edge of a succeeding turn, and a means for applying a bead of molten plastic material to said lapping edges of adjacent turns of ribbon, such that said bead welds said adjacent edges.

Preferably said apparatus further includes, a creasing means for forming a crease in said folded ribbon approximately midway across said ribbon, said crease being substantially parallel with said ribbon, and said creasing means positioned to crease said ribbon before being delivered around said former.

In a further aspect the invention may broadly be said to consist in an apparatus for continuously forming conduit comprising:

a means for supplying a thin polymer ribbon, a heating means for heating said polymer ribbon, a creasing means for forming a crease in said ribbon after being heated by said heating means, approximately midway across said ribbon, said crease being substantially parallel with said ribbon, a means for delivering said folded ribbon having "leading" and trailing" lateral edges, spirally around a former rotating and advancing said conduit, with the leading edge of each turn of ribbon overlapping the trailing edge of a previous turn of ribbon on the former and the trailing edge of each turn underlapping the leading edge of a succeeding turn, and a means for applying a bead of molten plastic material to said lapping edges of adjacent turns of ribbon, such that said bead welds said adjacent edges.

In a further aspect the invention may broadly be said to consist in a conduit formed by a method according to any one of the above paragraphs.

In a further aspect the invention may broadly be said to consist in a film formed by a method according to any one of the above paragraphs.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION OF THE PRIOR ART

The present invention relates to breathing conduits in general and in particular to improved methods of forming thin film spiral wound conduits. Consequently the present invention finds application in breathing conduits fabricated from a variety of materials which may include breathable and/or non-breathable materials (breathable materials being capable of transmitting water vapour).

Continuous Positive Airway Pressure (CPAP) systems or positive pressure ventilation systems that provide patients suffering from obstructive sleep apnoea (OSA) with positive pressure gases often use conduits similar to the prior art described. Often in these applications and in other medical applications, such as with assisted breathing, gases having high levels of relative humidity are supplied to patients and sometimes returned through conduits of a relatively restricted size. The aim of the present invention is to provide an alternative conduit that will withstand the stresses of high use, that is, being flexible yet not prone to breakage under axial stretching or movement.

The preferred conduits of the present invention are formed from a non-breathable material, such as a polymer plastic block formed into a homogeneous flat film. Examples of such polymer materials, are sold under the brands EXACT and EVOLUE.

In alternative forms of the conduit of the present invention, a conduit may be formed from a breathable material, such as a hydrophilic polyester block copolymer formed into a homogeneous flat film.

The following embodiments will be described with particular reference to an example non-breathable thin film wall construction from materials such as EVOLUE. It will be appreciated however, that in the following described embodiments the material used to form the conduit walls may be either breathable or non-breathable and may also include combinations of both breathable and non-breathable materials. It will be also appreciated for the following described embodiments that the film that is manipulated during the pre-forming stage of the method of the present invention, may be supplied initially either as a pre-formed film wound on to a spool or may alternatively be supplied directly from an extruder. It will also be appreciated by those skilled in the art that the materials supplied to a former used in the manufacture of the conduit may require guides and/or rollers in order to position the film accurately and provide the necessary tension.

It is preferred that the conduit wall be manufactured to have a relatively low wall thickness, so much so that the conduit wall membrane may be insufficiently sturdy to be self supporting. Spiral or helical reinforcing members are therefore provided as part of the tubular wall membrane to provide support. The helical or spiral supporting members are formed from polymer plastic materials and may be of the same material used in the wall of the conduit or any other compatible plastics material.

Figure 1:
FIG. 1 is a cross sectional side elevation of a conduit wall according to an embodiment of the prior art.

Referring to FIG. 1, the lay-up arrangement of a flexible breathing conduit known in the art is shown.

Pre-Forming of Film

The first step in the manufacture of the conduit of the present invention is the forming of a folded plastic film. The film may be formed with or without at least one integral electrical conductor. In other forms of the pre-formed film, the film may be formed with other material in place of the electrical conductor or conductors, such as a foam strip, a strip of conductive film or other conductive or insulative materials or a combination of both. The following describes by way of example, only one such form of the folded plastic film, i.e. with at least one integrally formed conductor.

Figure 2:
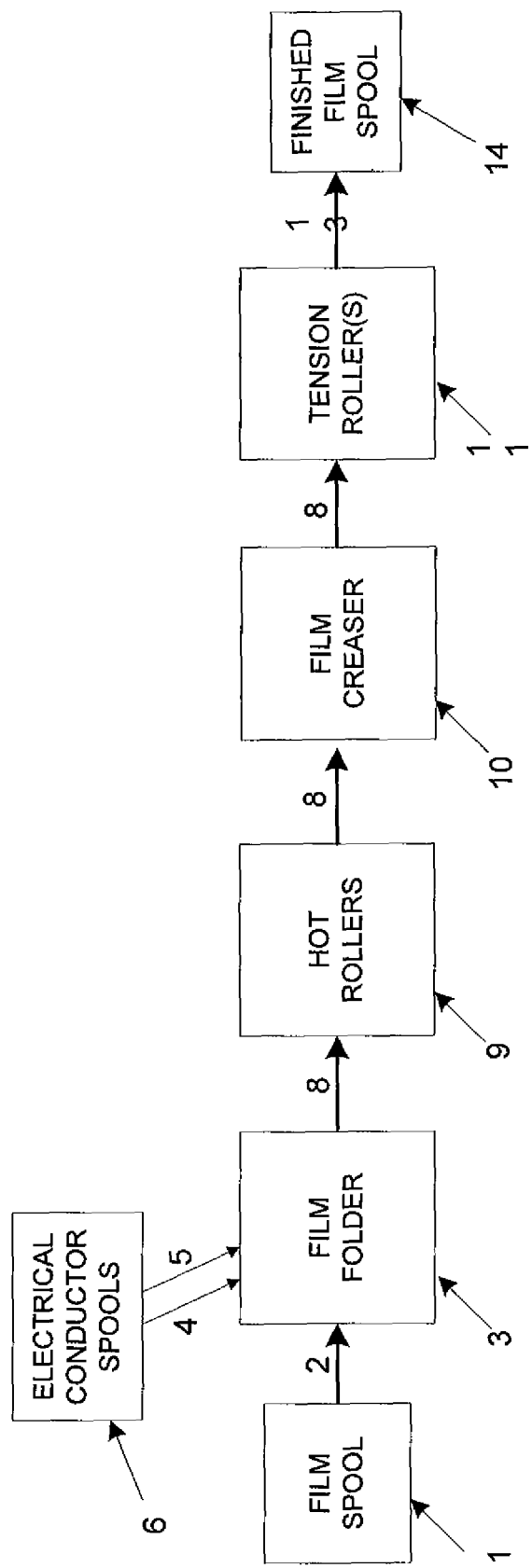
FIG. 2 is a flow diagram of the pre-forming of a narrow plastic film to be used in the manufacture of a conduit of an embodiment of the present invention.
Figure 4:
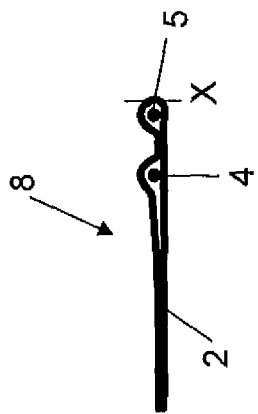
FIG. 4 is a cross sectional view of a pair of heater wires embedded in the film.
Figure 3:
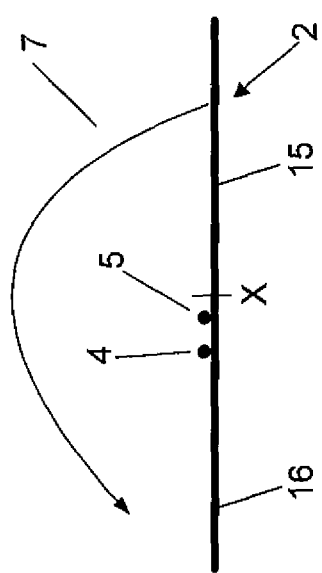
FIG. 3 is a cross sectional view of pre-forming a film, including a pair of heater wires, for use in forming the conduit of an embodiment of the present invention.

Referring to FIG. 2, a method of forming a plastic film including two parallel conductors is illustrated. Firstly, a plastic film 2, such as EVOLUE film, is supplied on a spool 1. Two electrical conductive wires 4, 5 are supplied on two spools 6. The film 2 and wires 4, 5 are simultaneously drawn from their respective spools 1, 6 and fed into the film folder 3. The film folder 3 preferably folds the film 2 in half with one of the two wires 5, running down the centre fold (X in FIGS. 3 to 6) in the film 2. FIG. 3 shows the film 2 and two wires 4, 5 prior to being fed into the film folder. Wires 4, 5 are accurately positioned via guides adjacent the fold position X and spaced apart on the surface of film 2. The arrow in FIG. 3, indicated as 7, shows one side of the film (the first side 15), which is folded over the second side 16 of the film 2, thereby encapsulating the wires 4, 5. The resulting double layered folded film 8 including two substantially parallel encapsulated conductors is shown in FIG. 4. The first lateral half 15, becomes the top layer of the film 8 and the second lateral half 16 becomes the bottom layer of the film 8.

Figure 15:
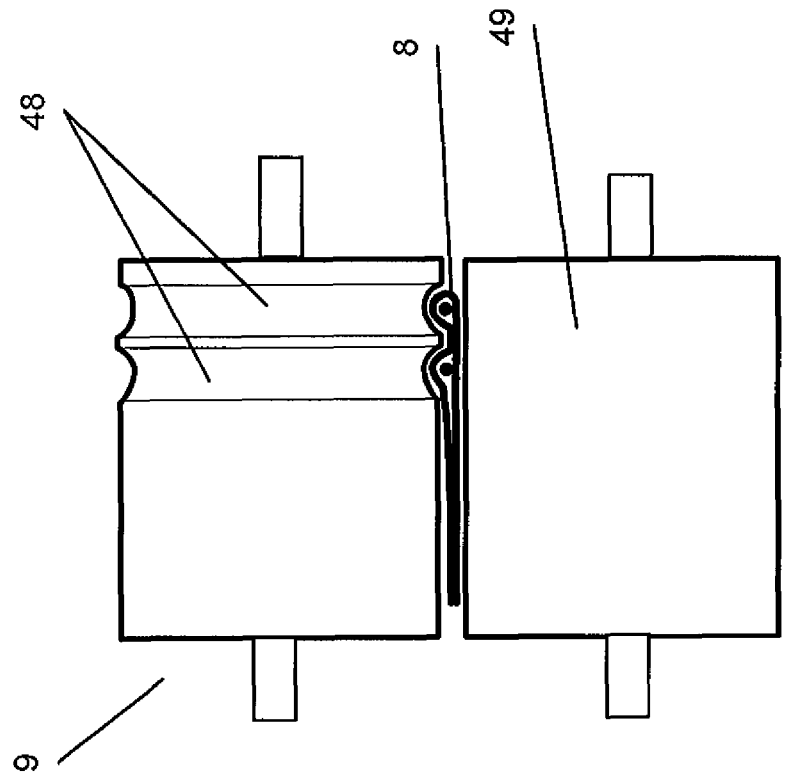
FIG. 15 is a view of the pre-formed film passing through the hot rollers.

With reference to FIGS. 2, 4 and 15, the resulting folded film 8 with encapsulated wires 4, 5 is then drawn between two hot rollers 9. The hot rollers have a surface temperature sufficient to soften the film and bond adjacent layers under pressure, for example approximately 90° C. and 120° C. Depending on the speed at which the film travels through the hot rollers 9, it may be necessary to have several stages of hot rollers to ensure that adequate welding occurs. Further, it may also be desirable to include secondary welding processes such as ultrasonic welding, or hot air welding. The hot rollers may be formed of any suitable material, for example aluminium. It has been found that an outer deformable surface layer 49, on at least one of the hot rollers, is useful to grip the film passing through the rollers and allow at least one of the roller surfaces to deform a little around the encapsulated wires. An example of a suitable material for this outer layer on the roller is silicon rubber. The hot rollers 9 are driven by a motor (not shown) to pull the film 2 and wires 4, 5 off their respective spools 1, 6 and draw the film 2 through the film folder 3. Heat from the rollers 9 softens the film (as the rollers temperatures are close to the film's melting temperature) while pressure exerted by the rollers as the folded film passed between them, presses the layers 15 and 16 of the folded film together causing the folded sides to fuse together, permanently encapsulating the wires therein.

In order to ensure that the encapsulated wires 4, 5 are maintained in their desired positions during the fusing process, at least one of the hot rollers includes a pair of grooves 48, adapted to receive wires 4. The position and dimensions of the grooves are such that they prevent the pressure exerted by the rollers on the film from flattening the film in the region of the conductive wires 4, 5 thus reducing undesired thinning of the polymer film around the encapsulated wires. These grooves 48 provide guidance for the wires 4, 5 ensuring they are positioned correctly with respect to the fold, and spaced the desired distance apart, for example, approximately 1 millimeter. It is preferred in the manufacture of folded film 8, that the film folder 3 is positioned so that the fold X runs on one of the grooves of the hot rollers 9, thereby positioning the first wire 5 into the fold X and the second wire 4, 1 millimeter away from the fold X. The film folder 3, is configured so that uneven film overlap is prevented. Such positioning of the film folder 3 is important to produce good quality pre-formed and folded film. In other, embodiments of the pre-formed and folded film the wires may be located at a distance from the fold or at different distances from one another.

Figure 5:
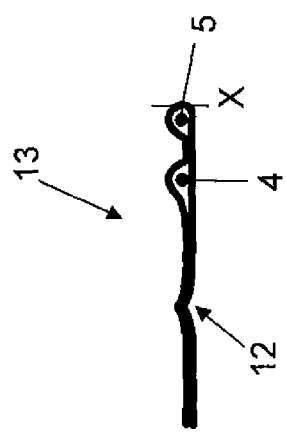
FIG. 5 is a cross sectional view of a folded film with a crease formed in it.
Figure 14:
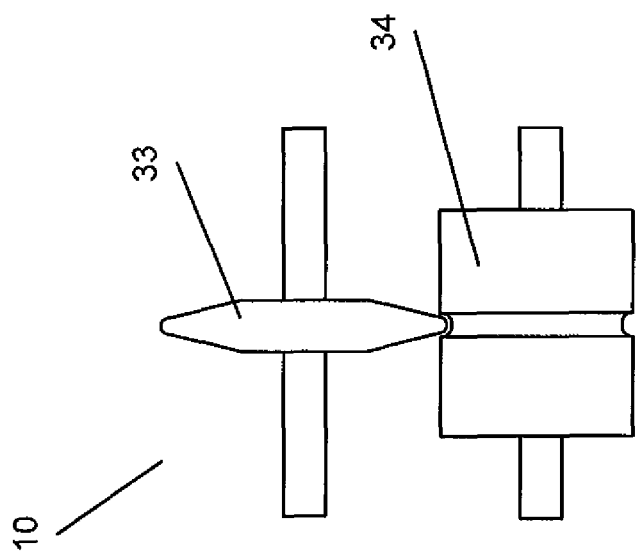
FIG. 14 is a front view of the film creaser showing the crease rollers.

The folded film 8 is then drawn from the hot rollers 9 and preferably passed through a film creaser 10 as shown in FIG. 14. The film creaser 10 consists of a roller 33 having a substantially v-shaped edge which runs in a correspondingly shaped groove in roller 34. The film creaser 10, creates a crease 12 in the folded film 8, as shown in FIG. 5. The crease 12 is formed in the folded film 8 subsequent to the hot rollers 9, while the film is still soft. The crease 12 may be formed approximately midway along the width of the folded film, in order to position the crease approximately midway between the turns of reinforcing bead in the finished conduit. The folded and creased film 13 is then uniformly drawn onto a finished film spool 14. The purpose of the crease 12 is to bias the conduit wall outward between the helical reinforcing bead. In use, when the conduit is contracted or bent, it is desirable to have the conduit wall portions between the bead, bulge outwards to reduce interference with the gasses flow within the conduit. The crease 12 encourages the conduit wall portions between the reinforcing bead to take up a regular folded position between the reinforcing bead 19 when the conduit is contracted or bent.

Figure 11:
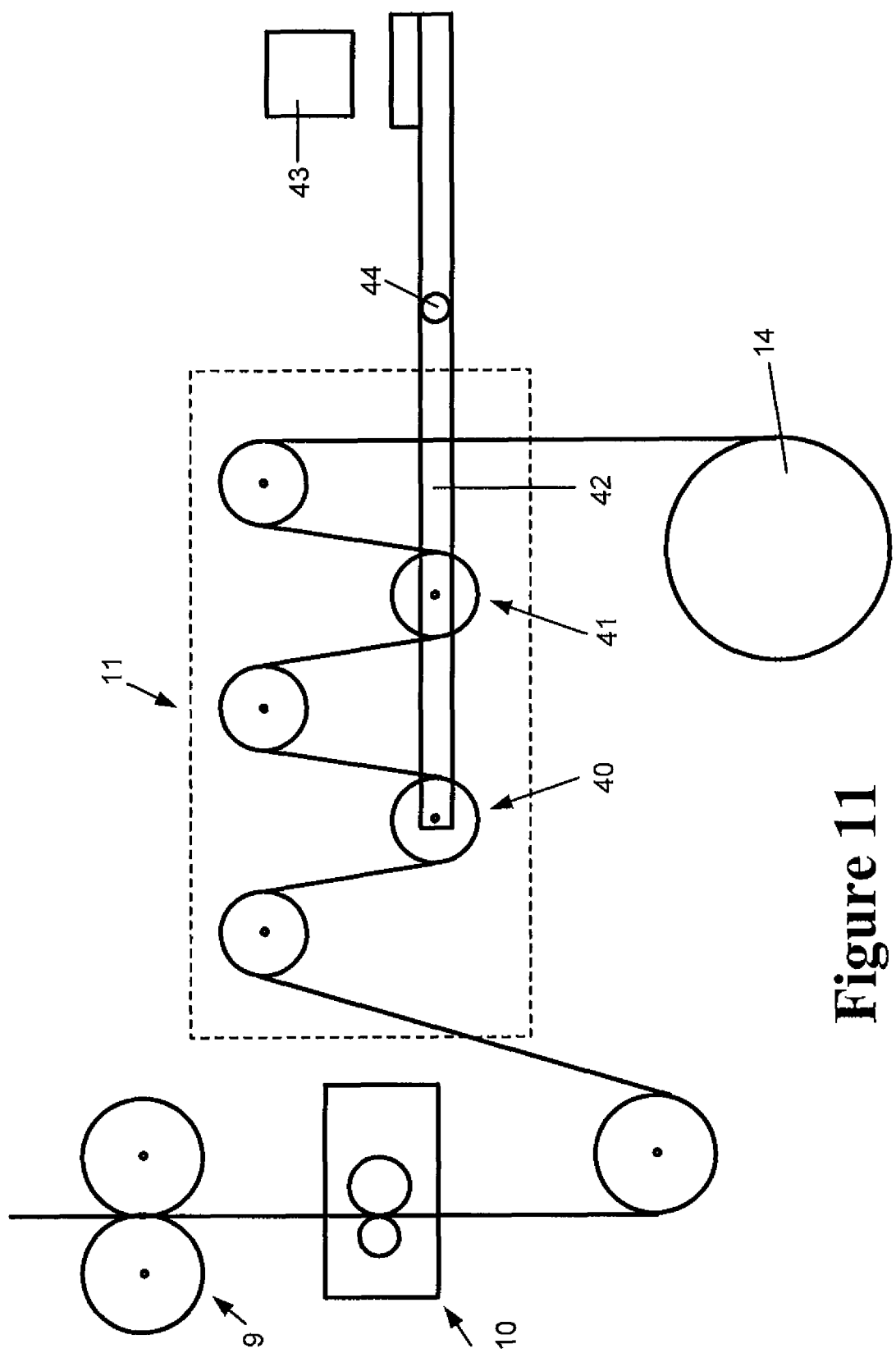
FIG. 11 is a diagrammatic side view of apparatus used to form the pre-formed film of the present invention.

Reference is now made to FIGS. 2 and 11. As the folded film is still soft when it comes out of the film creaser 10, the tension of the folded film 8 has to be controlled accurately so that the folded film 8 is not overstretched making the film thinner or narrower. Therefore, film 8 may be drawn through at least one tension roller 11, although more than one roller may be used. As shown in FIG. 11, two tension rollers 40, 41 are provided attached to an arm 42, and controlled by a position sensor 43. If the rollers 40, 41 are not in a position to provide the correct tension in the film 8, the rollers 40, 41 are adjusted until the correct film tension is applied. The rollers 40, 41 are attached to an arm 42 that rotates about a pivot point 44. When the tension of the film 8 increases and more force is placed on the rollers 40, 41 and arm 42, the arm 42 moves upwards out of a neutral position, (as shown on FIG. 11). The position sensor 43 located near the arm 42 detects the movement of the arm and causes the motor drawing the film through the rollers and onto the finished film spool 14 to decrease its speed, consequently reducing the pull on the film 8 through the tension rollers 40, 41. Conversely, if the position sensor 43 detects the movement of the arm 42 downwards out of the neutral position due to a reduction in the film tension, the sensor 43 causes the motor to increase its speed causing the film 8 to be drawn more quickly through the rollers 40, 41.

Figure 6:
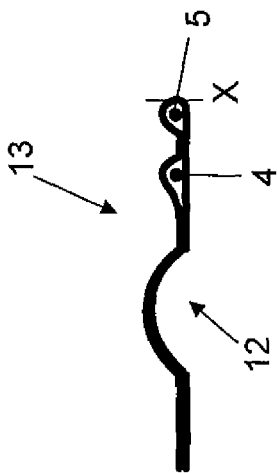
FIG. 6 is a cross section view of a folded film with a crease formed in it accordingly to a further embodiment.
Figure 16:
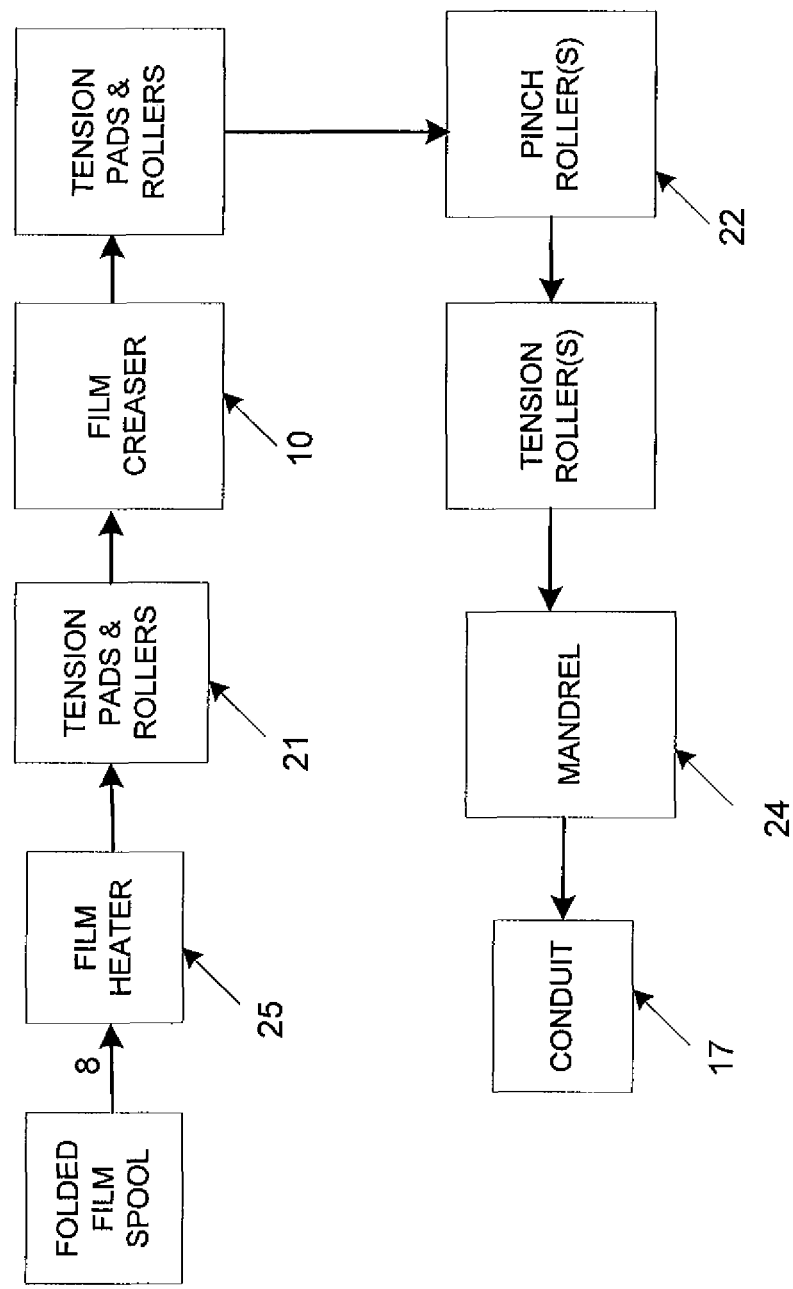
FIG. 16 is a flow diagram showing steps in the method of manufacturing conduit according to a further embodiment of the present invention.

It has been found that varying the shape of crease 12 (as shown in FIG. 5) maybe advantageous for influencing the conduit wall to deflect in a desirable manner. For example it has been found that a wider more rounded arcuate crease (such as shown in FIG. 6) may be more effective in ensuring that the conduit wall behaves as desired when the conduit is constricted axially or bent. It will be appreciated by those in the art that the profile of crease rollers 33 and corresponding roller 34 (as shown in FIG. 14) will influence the shape of crease 12. Further it will also be appreciated that crease roller 33 may be wider than shown and also include portions for guiding the outer regions of folded film 8 to reduce the tendency of the film to curl in an undesirable manner during creasing. It has also been found that forming crease 12 after the film is folded and fused, but before the pre-formed and folded film is wound onto a storage spool 14, may lead to a certain amount of flattening out of crease 12 while on the storage spool. It has been found to be advantageous to delay the crease forming process until immediately before forming the conduit. In this alternative embodiment of the method, the pre-formed tape 8 is folded (with or without encapsulated conductors) and fused, before being wound onto a storage spool, and after sufficient cooling. With reference to FIG. 16, before the conduit forming process described below is commenced, the folded film 8 (but not creased), is heated and fed through the film creasing apparatus 10 described above. In a similar manner to described above, the film may be passed through a series of tension rollers and/or pinch rollers in order to control the tape forming and winding process. After the film has passed through the film creaser 10, the film is allowed to cool and harden a little before being fed onto the forming mandrel 24 and the conduit 17 is formed. In other embodiments of the pre-formed film of the present invention, a film may be formed that does not have the conductive wires encapsulated within it. This form of the film could be used in conduits not requiring heating elements.

It will be appreciated that the method of forming a conduit described herein discloses both a pre-formed and folded tape encapsulating one or more elements such as conductors or insulators) as well as a method of creasing a pre-formed tape at sometime before supplying it to a forming mandrel. However, it will also be appreciated that the pre-formed film method and the pre-creasing method may both be applied to a conduit forming method or maybe applied individually.

Conduit Forming

A conduit formed using a pre-formed film such as those discussed above will now be described in more detail. It will be appreciated that manufacture of heated conduits (including at least one conductor) is achieved by using a pre-formed film as described above including at least one imbedded conductor. Similarly, the manufacture of non heated conduits is achieved by employing a pre-formed film without any encapsulated conductors.

The following description does not distinguish between a pre-formed film with or without encapsulated material. Therefore, when "film" or "pre-formed film" is referred to below it will be appreciated that the film may or may not include embedded conductors or insulative materials or both.

Figure 7:
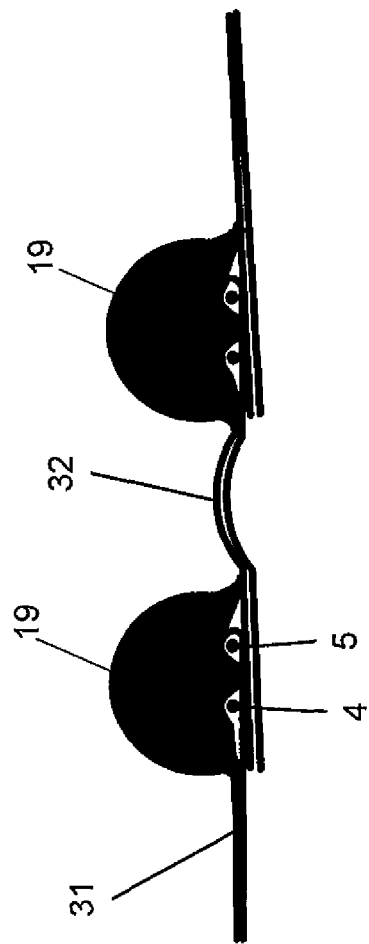
FIG. 7 is a cross sectional view of a conduit wall including a pair of heater wires, formed from the pre-formed film shown in FIG. 4.
Figure 8:
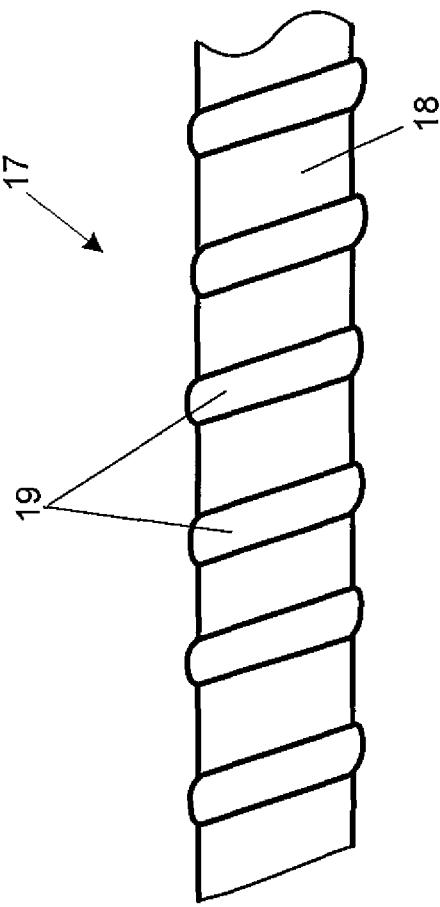
FIG. 8 is a side elevation of a conduit according to an embodiment of the present invention having an outer reinforcing bead.

FIG. 8 illustrates a conduit 17 formed from a film as described above and using the conduit forming method as described below. It will be appreciated that the figures (for example FIG. 7) are illustrative and may show gaps or spaces between layers of film and reinforcing bead that are not actually present in the finished product but are shown in the figures to distinguish layers. The conduit may be used as a transport path or passageway for supplying gases to a patient and has a thin film flexible wall. The film, such as the pre-formed film described above, is arranged in a spiral or helix such that the edge portions of adjacent layers overlap and form the wall 18 of the conduit or tube 17. A helical reinforcing bead 19 of polymer material is extruded over the overlapping portions of adjacent winds of film to bond the overlapping portions of film to form a continuous conduit or tube 17.

FIG. 7 illustrates a similar conduit to that of FIG. 8, but having integral conductors formed into the conduit wall. FIG. 7 shows a cross section of a folded film including two encapsulated conductive wires 4, 5. The bead 19 is extruded onto the overlapping portions of adjacent layers 31, 32 (having the encapsulated conductive wires 4, 5). The molten bead 19 bonds the two layers together.

Figure 9:
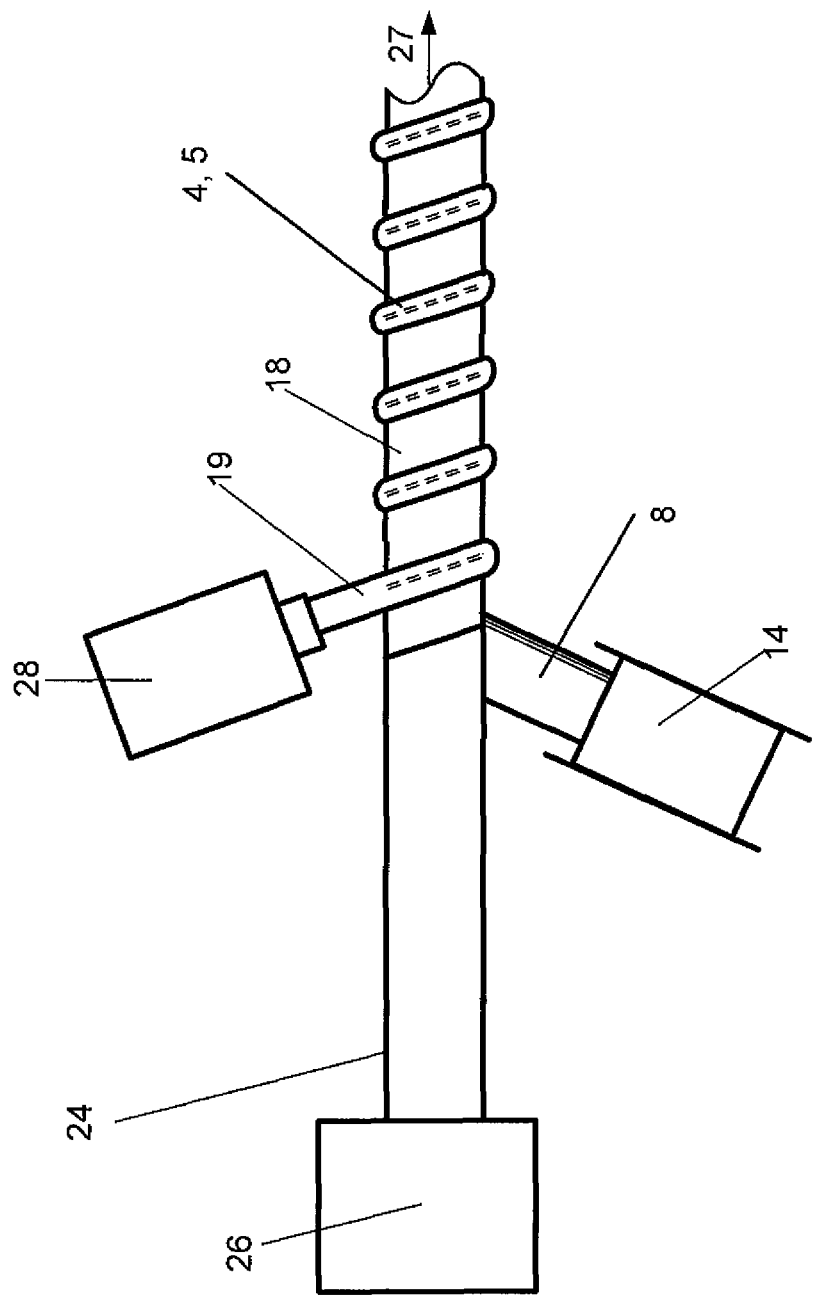
FIG. 9 is a plan view of a conduit forming device for forming a conduit according to an embodiment of the present invention.
Figure 10:
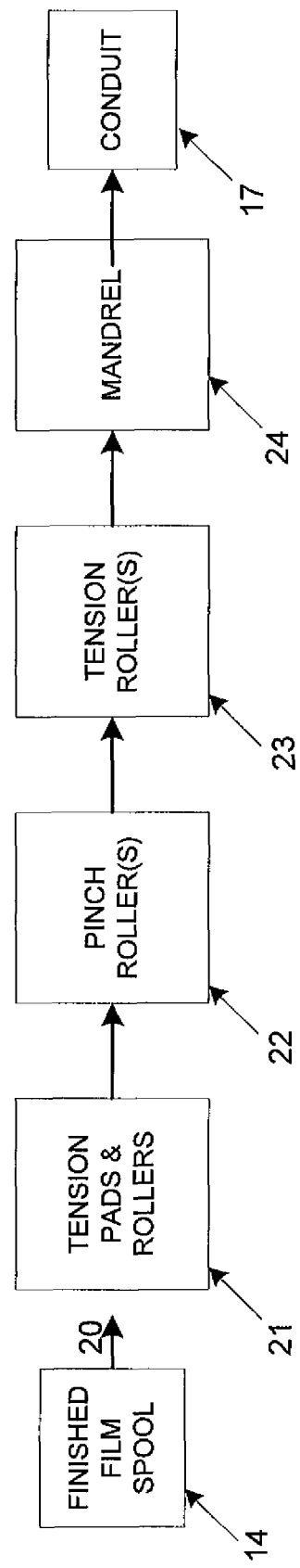
FIG. 10 is a flow diagram of the steps in the method of manufacturing a conduit according to an embodiment of the present invention.
Figure 12:
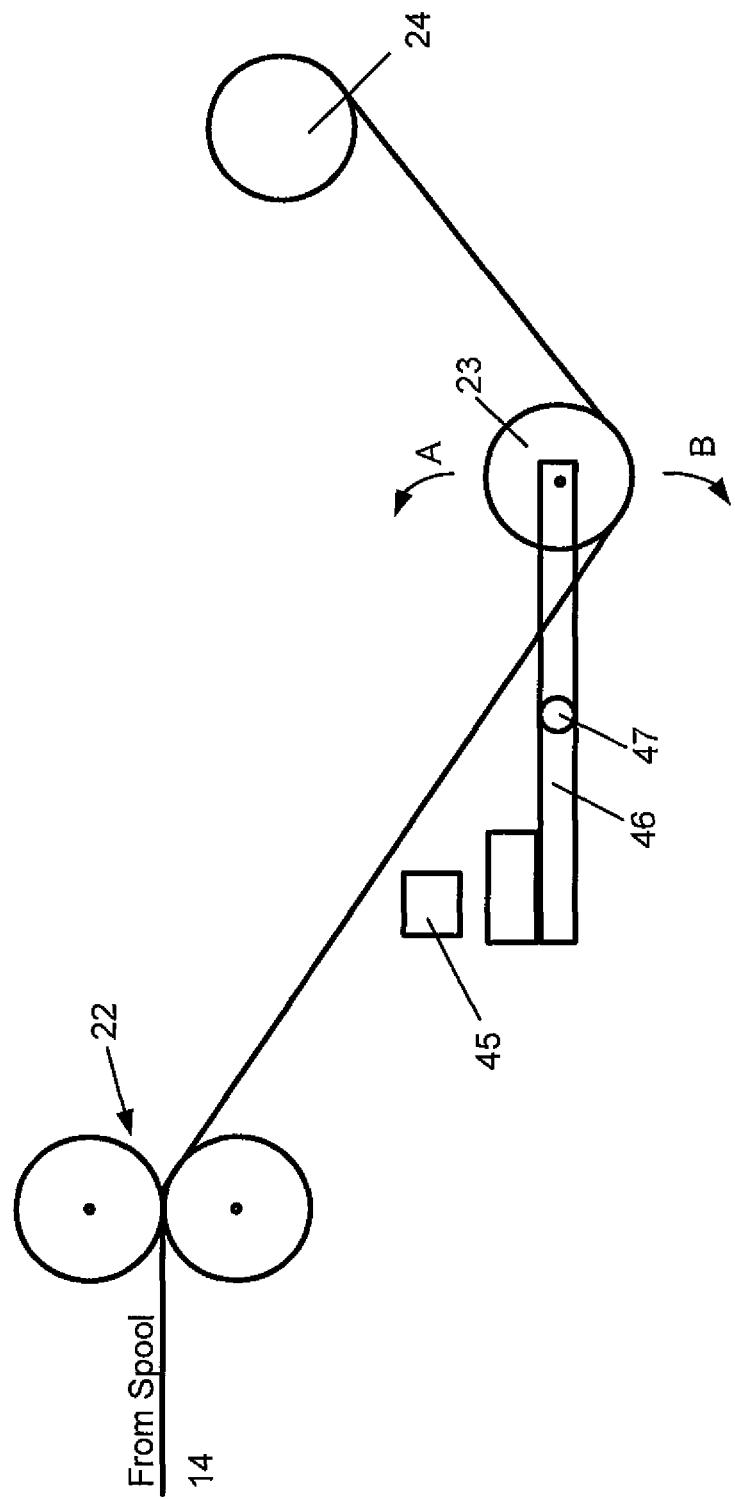
FIG. 12 is a diagrammatic end view of apparatus used to form conduit according to an embodiment of the present invention.

An example of the forming apparatus suitable for manufacturing the conduits of FIG. 7 or FIG. 8 is shown in FIGS. 9 and 12. FIG. 10 illustrates the steps in the conduit forming process of the present invention. The spool 14 of pre-formed film as described above is mounted onto a frame (not shown) of the conduit forming apparatus. The film (which may include wires 4, 5) is drawn from the spool 14 through various tension pads and rollers 21, then through pinch rollers 22. Next the film passes through at least one tension roller 23 and is fed onto a mandrel or former 24.

With reference to FIG. 9, the former, preferably of a known type, includes a plurality of rotating rods or cables arranged around a central support rod. The rods or cables extend from and are rotated by a gearbox within a machine stock 26. At least in the conduit forming region the rotating rods follow a helical path. The pitch angle of the rods relative to the support rod controls the pitch angle of the conduit being formed. An example of such a former is a spiral pipeline mandrel available from OLMAS SRL of Italy.

The conduit being formed on the former is rotated and advanced in the direction of arrow 27 by the movement of the rotating cables. The advance speed of the former is selected relative to the rotational speed of the cables and is dependent on the pitch of the helical laying of the film on to the former, such that adjacent turns of the film narrowly overlap. The spool 14 of pre-formed film 8 as described above is eventually fed (after being fed through tension rollers and the like) onto the former (mandrel 24) in a helical fashion by action of the former. The pitch of the helical disposition of film 8 is slightly less than the width of film 8 and results in an overlap of approximately 2 millimeters. The helical deposition of film 8 forms the wall 18 of the conduit shown in FIG. 8. An extruder 28 extrudes the bead 19 of polymer material onto the overlap of the film winds. The rotating mandrel 24 draws the molten bead 19 over the overlapping portions of adjacent winds of film 8, the bead is sufficiently heated to weld to the layers of film 8. In one preferred embodiment of the present invention the bead 19 is extruded at approximately 250° C. providing enough heat to thermally bond the layers of film together. The conduit formed according to this method has an approximate internal diameter of 19 millimeters. It will be appreciated by those skilled in the art that alternative or secondary welding processes may also be employed, for example ultrasonic welding, or hot air welding.

It will be appreciated however that the method of forming is also suitable for both larger and smaller conduits. If the conduit is a heated type having encapsulated conductive wires (see FIG. 7), the extruder 28 is positioned so that the bead 19 is drawn on to the correct position to completely bond the overlapping film together and to encapsulate the wires. In both heated and non-heated conduits, the bead 19 is shaped to assist in the forming of the conduit.

Figure 13:
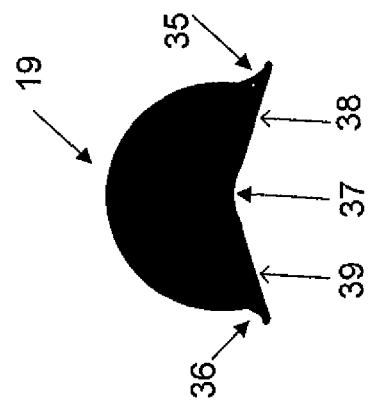
FIG. 13 is a cross sectional view of the reinforcing bead extruded onto the conduit on the mandrel.

With reference to FIGS. 7 and 13, the bead 19 is concave nearer the middle of its underside, and edges 38, 39 are angled out to the periphery of the bead 19. The concave shaped underside 37 helps to provide guidance for the laying of the bead 19. The bead tends to follow the raised portions of film created by the encapsulated wires. The straight sides 38, 39 of the underside of the bead also help to keep the film 20 flat and become substantially horizontal during the forming process. The bead 19 may be extruded with indented sides 35, 36 toward the base of the bead. After extrusion, the bead 19 tends to change shape or "swell". Indented sides 35 and 36 may be provided in order to better control the final shape of reinforcing bead 19 in the finish conduit.

When the conduit thus formed is contracted longitudinally, the crease 12 formed in the film, as shown and described in relation to FIG. 5 and 6, tends to cause a folding in the conduit outwards between the reinforcing bead 19 and moves the film out of the gases path through the conduit. The bead width and height are chosen to give an adequate crush strength and to allow enough space for the film to fold upwards between the bead, while retaining its general shape and proportions.

Referring back to FIGS. 10 and 12, the frame of the conduit forming apparatus of the present invention has many degrees of freedom to allow adjustment of the angle that the film is fed onto the mandrel 24. The frame includes a set of set of pinch rollers 22 mounted thereon, which pull the film from it's spool 14, through at least one tensioning pad and around at least one roller 21, which are also mounted on the frame of the conduit forming apparatus. The film 20 is then fed around at least one tension roller 23 and then onto the mandrel 24.

A difference in speed between the pinch rollers 22 and the cables on the mandrel 24 may create tension in the film. The film tension is important to maintain the stability of the film on the mandrel 24 and also to allow the film wall to fold upwards between the reinforcing bead 19, when the conduit is bent or contracted.

The tension roller 23 is controlled by a sensor 45 and arm 46, in a similar manner as described previously for the pre-formed film method. If the tension in the film 20 increases, roller 23 (attached to the arm 46) and arm 46, pivoting about a pivot point 47, move upwards in the direction of arrow A. The position sensor 46 senses the change in position of the arm 46 and thus roller 23 and the motor driving the pinch rollers 22 increase the speed at which the film is drawn from the spool 14 and the tension in the film reduces causing the roller 23 and arm 46 to move back to the central position as shown in FIG. 12. Conversely, if the tension of the film decreases the arm 46 and roller 23 move downwards in the direction of arrow B. The position sensor 45 senses this change in position and causes the motor driving the pinch rollers 22 to decrease the speed at which the film is drawn from the spool 14. The sensor 45, pivotable arm 46 and roller 23, ensure that a constant tension of the film is maintained so that the film 20 being wound onto the mandrel 24 has a constant overlap.

The mandrel 24, may include air or water cooling or both, to cool the conduit as it is formed on the mandrel 24 to ensure that the bead 19 does not melt through both the overlapping layers of film. Further cooling, external to the conduit, may also be provided. Internal air cooling may be provided by stainless steel needle like tubing on the mandrel, which spray several fine jets of air onto the inside of the tube. External air-cooling may be provided by a series of air jets that spray a blade of air onto the outside of the tubing.

The mandrel 24 will now be described in more detail. Mandrel 24 includes six stainless steel cables, all of which are rotated at the same speed. The cables are located in the mandrel 24 within undercut grooves, machined into the stainless steel mandrel in a helical configuration. The mandrel 24, preferably made of stainless steel, has scallops machined into it between the cable grooves to provide a clearance so that the film rests on the cables, rather than the mandrel 24. A groove is also machined into the centre of these scallops to provide a space for the air cooling tubing. The mandrel may also be water cooled, and include monitoring of the water flow rate, to ensure that there is sufficient cooling.

The cables provide the drive to pull the film onto the mandrel 24 as described above. The helical angle of these cables is important to create the correct amount of overlap of the film. With the angle of the cables set at 6.6 degrees to the horizontal, the film is drawn onto the mandrel 24 and is wrapped around it in a helix as described above. The set angle causes the film to overlap by approximately 2 millimeters.

With reference to FIG. 7, overlap of the film layers under the wires 4, 5 provides three thicknesses of film between the wires and inside the conduit. This prevents the wires from being melted out and exposed on the inside of the conduit, and provides a thicker surface to retain the wires for increased durability. The angle of the film being fed onto the mandrel ensures a conduit is formed with a particular pitch, which has been found to give a good compromise between the crush strength and the amount of film between the bead.

The method of pre-forming the film of the present invention could be extended to include additional folding of the initial film to produce films of more layers. Alternatively, more than one film could be used in the formation of the conduit of the present invention to increase the thickness of the conduit wall and thus the walls strength, yet still providing a conduit that is flexible.

Heated conduits formed by the method described above may reduce the build up of condensation in the conduit and may also offer a means to maintaining the temperature of humidified gases flowing through the conduit. Heated conduits are used commonly as gases transportation pathways in applications such as for Continuous Positive Airway Pressure (CPAP) therapy. In such conduits where the pathway includes conductive wires to heat gases flowing through the pathway, the corresponding connectors, at least at one end of the conduit, will include an electrical connection suitable for connection with the humidified gases source in order to supply electrical energy to the conduit heater wires.

The pre-forming of a tape with embedded heater wire, in accordance with one aspect of the present invention, confers the advantage of accurately locating the wires relative to the tape edge in a process that is more easily controlled than when applying the wires directly to the tube forming mandrel.

The provision of a crease in the tape, in accordance with another aspect of the present invention, confers the advantage of defining the preferred deformation modes of the conduit wall, such that the tube wall will predominantly be caused to bulge outwards on bending or contraction of the conduit.

The invention claimed is:

1. A method of continuously forming a breathing conduit comprising:

providing a thin polymer ribbon, positioning at least a first conductor and a second conductor adjacent to and substantially parallel with said ribbon, said first conductor and said second conductor being separated by a controlled spacing, folding said ribbon substantially in half parallel with said ribbon such that said first and second conductors are adjacent to, and encapsulated in said fold, and thermally welding said folded ribbon to permanently encapsulate said first and second conductors, supplying said folded ribbon having "leading" and "trailing" lateral edges, spirally around a former rotating and advancing said conduit, with the leading edge of each turn of ribbon overlapping the trailing edge of a previous turn of ribbon on the former and the trailing edge of each turn underlapping the leading edge of a succeeding turn, and applying a bead of molten plastic material over both said lapping edges of adjacent turns of ribbon and said first and second conductors, such that said bead welds said adjacent edges.

2. A method of continuously forming a breathing conduit as claimed in claim 1, wherein said first and second conductors are a pair of conductors, and said conductors are positioned parallel and closely spaced and said ribbon is folded adjacent one of said first and second conductors; such that said first conductor is adjacent to and encapsulated in said fold, and said second conductor is spaced from said first conductor and encapsulated in said fold.

3. A method of continuously forming a breathing conduit as claimed in claim 1, wherein said thermal welding includes passing said folded ribbon between a pair of heated rollers, said rollers applying pressure to squeeze said folded ribbon together.

4. A method of continuously forming a breathing conduit as claimed in claim 3, wherein at least one of said rollers includes a groove for at least partially receiving each of said first and second conductors and a layer of ribbon over it.

5. A method of continuously forming a breathing conduit as claimed in claim 1 wherein said method further comprises forming a crease substantially midway along said folded ribbon, said crease being substantially parallel with said ribbon;

forming said crease while said ribbon is softened following said thermal welding occurring.

6. A method of continuously forming a breathing conduit as claimed in claim 2 wherein said method further comprises forming a crease substantially midway along said folded ribbon, said crease being substantially parallel with said ribbon;

forming said crease while said ribbon is softened following said thermal welding occurring.

7. A method of continuously forming a breathing conduit as claimed in claim 6, wherein said crease is formed by passing said folded ribbon through at least one set of crease rollers, said crease rollers in a creasing region shaped according to the profile of said crease.

8. A method of continuously forming a breathing conduit as claimed in claim 6, wherein said crease is substantially v-shaped.

9. A method of continuously forming a breathing conduit as claimed in claim 1, wherein said controlled spacing comprises 1 mm between said first conductor and said second conductor.

10. A method of continuously forming a breathing conduit as claimed in claim 8, wherein said substantially v-shaped crease comprises an inverted v.

11. A method of continuously forming a breathing circuit as claimed in claim 1, wherein thermally welding said folded ribbon comprises thermally welding said folded ribbon such that said first conductor is isolated from said second conductor by said folded ribbon.

12. A method of continuously forming a breathing circuit as claimed in claim 1 further comprising accurately positioning said first and second conductors via guides adjacent to a center fold location along said ribbon.

13. A method of continuously forming a breathing circuit as claimed in claim 1 further comprising positioning said first and second conductors over a lapping portion of the adjacent turn of ribbon such that three layers of ribbon are positioned between said first and second conductors and a passage defined by the breathing circuit.

14. A method of continuously forming a breathing circuit as claimed in claim 1, wherein thermally welding said folded ribbon comprises applying pressure to said ribbon to each side of said first and second conductors without exerting pressure on portions of the ribbon overlying and underlying said first and second conductors.

15. A method of continuously forming a breathing circuit as claimed in claim 1, wherein uneven film overlap is prevented.

16. A method of continuously forming a breathing circuit as claimed in claim 1 further comprising forming a crease within the folded and welded ribbon and then controlling a tension applied to the film after the crease has been formed such that the folded and welded ribbon is not overstretched.

17. A method of continuously forming a breathing circuit as claimed in claim 1 further comprising forming a crease within the folded and welded ribbon and then allowing the creased, folded and welded ribbon to cool prior to supplying said folded ribbon spirally around the former.

* * * * *